United States Patent
Zanella, Sr. et al.

(10) Patent No.: US 10,627,379 B2
(45) Date of Patent: Apr. 21, 2020

(54) COMPARATIVE DIAGNOSTICS FOR CATALYTIC STRUCTURES AND COMBUSTIBLE GAS SENSORS INCLUDING CATALYTIC STRUCTURES

(71) Applicant: MSA TECHNOLOGY, LLC, Cranberry Township, PA (US)

(72) Inventors: Mark Flori Zanella, Sr., Chicora, PA (US); Meghan E. Swanson, Pittsburgh, PA (US); Daniel Santoro, Pittsburgh, PA (US)

(73) Assignee: MSA TECHNOLOGY, LLC, Cranberry Township, PA (US)

( * ) Notice: Subject to any disclaimer, the term of this patent is extended or adjusted under 35 U.S.C. 154(b) by 357 days.

(21) Appl. No.: 15/597,933

(22) Filed: May 17, 2017

(65) Prior Publication Data

US 2018/0335412 A1    Nov. 22, 2018

(51) Int. Cl.
*G01N 27/16* (2006.01)
*G01N 7/00* (2006.01)
(Continued)

(52) U.S. Cl.
CPC ....... *G01N 33/0027* (2013.01); *G01N 27/124* (2013.01); *G01N 27/16* (2013.01);
(Continued)

(58) Field of Classification Search
CPC .. G01N 33/0027; G01N 27/124; G01N 27/16; G01N 33/0016; G01N 33/0031;
(Continued)

(56) References Cited

U.S. PATENT DOCUMENTS 4,533,520 A    8/1985   Bossart
4,627,269 A    12/1986  Forster
(Continued)

FOREIGN PATENT DOCUMENTS

EP    0500598 B1    3/1997
GB    1550615       8/1979
(Continued)

OTHER PUBLICATIONS

Cullis, C.F., and Firth, J.G., Eds., Detection and Measurement of Hazardous Gases, Heinemann, Exeter, 29 (1981).
(Continued)

*Primary Examiner* — Brian J. Sines
(74) *Attorney, Agent, or Firm* — Bartony & Associates, LLC

(57) ABSTRACT

A combustible gas sensor for detecting an analyte gas includes a first element including a first electric heating element, a first support structure on the first electric heating element and a first catalyst supported on the first support structure and electronic circuitry in electrical connection with the first element. The electronic circuitry is configured to operate in a first mode in which the first element is operated at a first temperature at which the first catalyst catalyzes combustion of the analyte gas, and in a second mode wherein the first element is operated at a second temperature which is below the temperature at which the first catalyst catalyzed combustion of the analyte gas but at which Joule heating of the first element occurs. The electronic circuitry is further configured to measure a variable in the second mode related to a mass of the first element.

27 Claims, 11 Drawing Sheets

(51) Int. Cl.
*G01N 21/00* (2006.01)
*G01N 27/00* (2006.01)
*G01N 31/00* (2006.01)
*G01N 33/00* (2006.01)
*G01N 27/12* (2006.01)

(52) U.S. Cl.
CPC ..... *G01N 33/0016* (2013.01); *G01N 33/0031* (2013.01); *G01N 33/007* (2013.01)

(58) Field of Classification Search
CPC ........ G01N 33/007; G01N 7/00; G01N 21/00; G01N 27/00; G01N 31/00; G01N 33/00
USPC ...... 422/83, 93, 94, 95, 96, 97, 98; 436/152, 436/139, 143, 144
See application file for complete search history.

(56) References Cited

U.S. PATENT DOCUMENTS

| | | | |
|---|---|---|---|
| 5,528,225 | A | 6/1996 | Sakai |
| 5,599,584 | A * | 2/1997 | Champney, Jr. ....... G01N 27/16 427/245 |
| 5,780,715 | A | 7/1998 | Imblum |
| 6,131,438 | A | 10/2000 | Zanini-Fisher |
| 6,163,347 | A * | 12/2000 | Fajardo .................... G06T 5/50 348/584 |
| 6,705,152 | B2 | 3/2004 | Routkevitch |
| 8,826,721 | B2 | 9/2014 | Zanella, Sr. |
| 9,528,957 | B2 * | 12/2016 | Scheffler ............... G01N 27/26 |
| 2002/0146352 | A1 | 10/2002 | Wang |
| 2008/0034841 | A1 | 2/2008 | Bahs |
| 2011/0100090 | A1 | 5/2011 | Zanella, Sr. |
| 2012/0318037 | A1 | 12/2012 | Lee |
| 2014/0273263 | A1 | 9/2014 | Zanella, Sr. |
| 2018/0128763 | A1 | 5/2018 | Swanson |

FOREIGN PATENT DOCUMENTS

| | | |
|---|---|---|
| JP | 2000039413 | 2/2000 |
| WO | WO2018085026 | 5/2018 |
| WO | WO2018212965 | 11/2018 |
| WO | WO2018212966 | 11/2018 |

OTHER PUBLICATIONS

Firth, J.G. et al., Combustion and Flame 21, 303 (1973).
Mosely, P.T. and Tofield, B.C., ed., Solid State Gas Sensors, Adams Hilger Press, Bristol, England (1987).

* cited by examiner

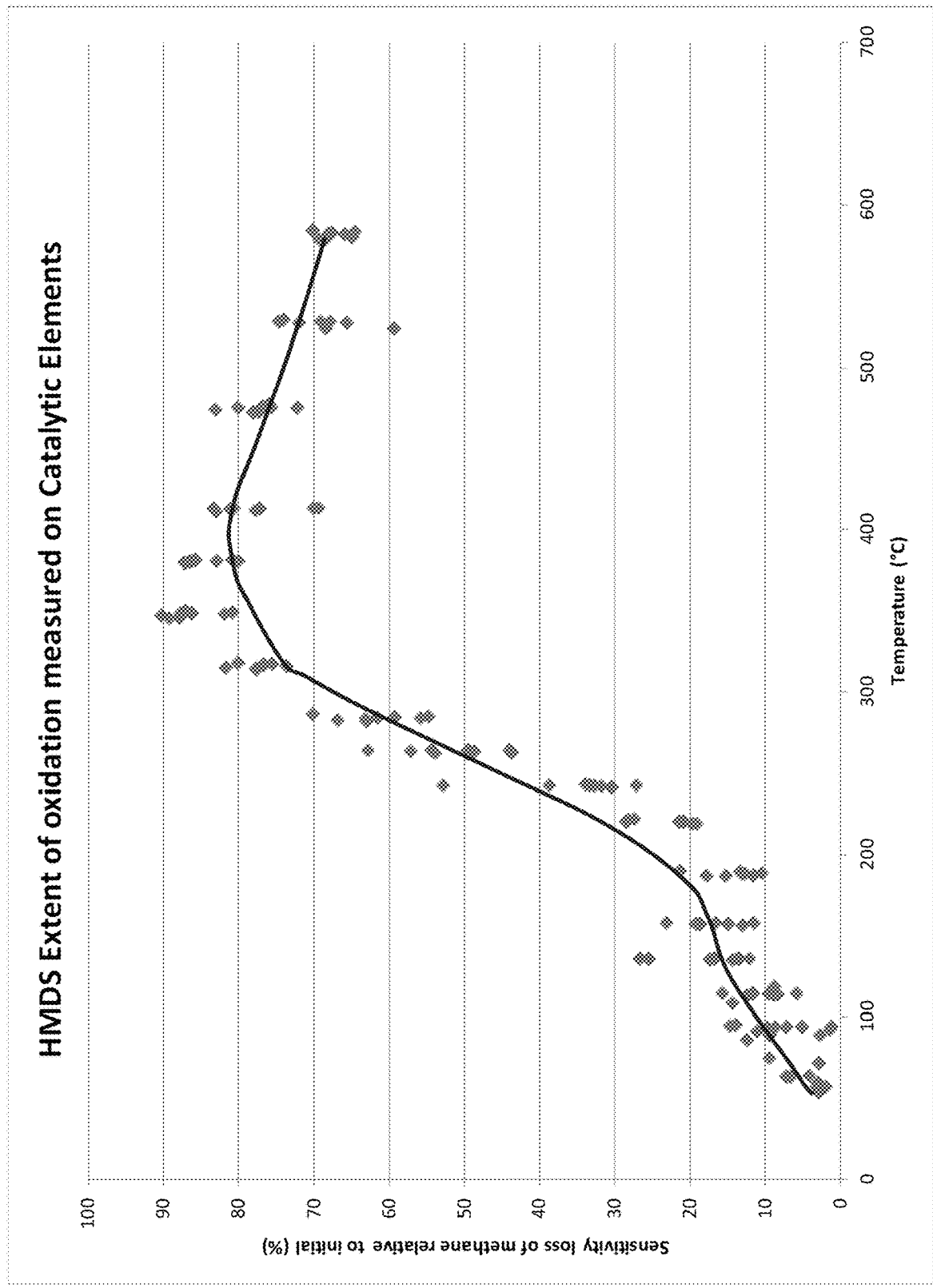

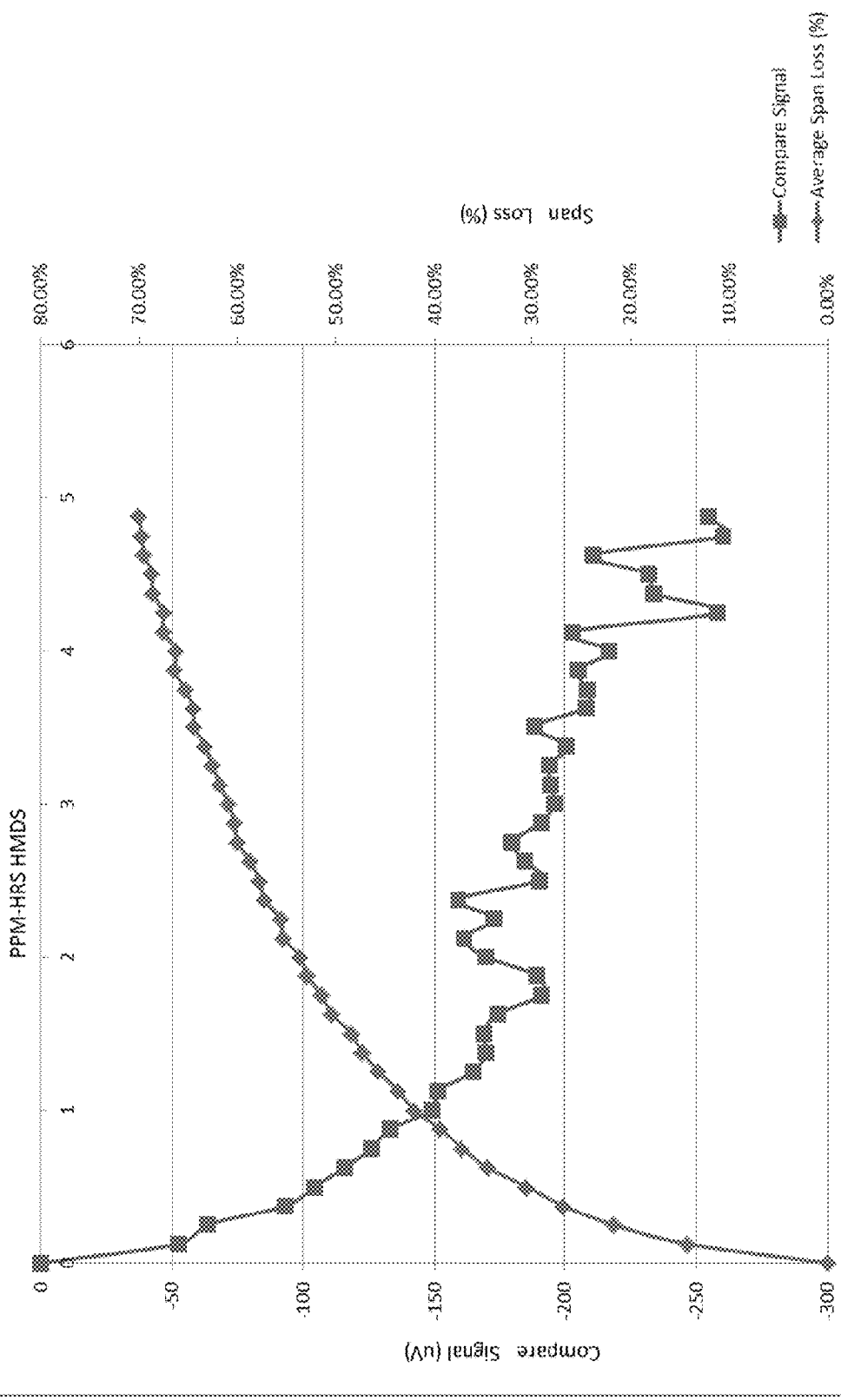

COMPARATIVE DIAGNOSTICS FOR CATALYTIC STRUCTURES AND COMBUSTIBLE GAS SENSORS INCLUDING CATALYTIC STRUCTURES

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Catalytic or combustible (flammable) gas sensors have been in use for many years to, for example, prevent accidents caused by the explosion of combustible or flammable gases. In general, combustible gas sensors operate by catalytic oxidation of combustible gases.

The operation of a catalytic combustible gas sensor proceeds through electrical detection of the heat of reaction of a combustible gas on the oxidation catalyst, usually through a resistance change. The oxidation catalysts typically operate in a temperature above 300° C. to catalyze combustion of an analyte (for example, in the range of 350 to 600° C. temperature range for methane detection). Therefore, the sensor must sufficiently heat the sensing element through resistive heating. In a number of combustible gas sensors, the heating and detecting element are one and the same and composed of a platinum alloy because of its large temperature coefficient of resistance and associated large signal in target/analyte gas. The heating element may be a helical coil of fine wire or a planar meander formed into a hotplate or other similar physical form. The catalyst being heated often is an active metal catalyst dispersed upon a refractory catalyst substrate or support structure. Usually, the active metal is one or more noble metals such as palladium, platinum, rhodium, silver, and the like and the support structure is a refractory metal oxide including, for example, one or more oxides of aluminum, zirconium, titanium, silicon, cerium, tin, lanthanum and the like. The support structure may or may not have high surface area (that is, greater than 75 $m^2/g$). Precursors for the support structure and the catalytic metal may, for example, be adhered to the heating element in one step or separate steps using, for example, thick film or ceramic slurry techniques. A catalytic metal salt precursor may, for example, be heated to decompose it to the desired dispersed active metal, metal alloy, and/or metal oxide.

As illustrated in FIGS. 1A and 1B, a number of conventional combustible gas sensors such as illustrated sensor 10 typically include an element such as a platinum heating element wire or coil 20 encased in a refractory (for example, alumina) bead 30, which is impregnated with a catalyst (for example, palladium or platinum) to form an active or sensing element, which is sometimes referred to as a pelement 40, pellistor, detector or sensing element. A detailed discussion of pelements and catalytic combustible gas sensors which include such pelements is found in Mosely, P. T. and Tofield, B. C., ed., *Solid State Gas Sensors*, Adams Hilger Press, Bristol, England (1987). Combustible gas sensors are also discussed generally in Firth, J. G. et al., *Combustion and Flame* 21, 303 (1973) and in Cullis, C. F., and Firth, J. G., Eds., *Detection and Measurement of Hazardous Gases*, Heinemann, Exeter, 29 (1981).

Bead 30 will react to phenomena other than catalytic oxidation that can change its output (i.e., anything that changes the energy balance on the bead) and thereby create errors in the measurement of combustible gas concentration. Among these phenomena are changes in ambient temperature, humidity, and pressure.

To minimize the impact of secondary effects on sensor output, the rate of oxidation of the combustible gas may, for example, be measured in terms of the variation in resistance of sensing element or pelement 40 relative to a reference resistance embodied in an inactive, compensating element or pelement 50. The two resistances may, for example, be part of a measurement circuit such as a Wheatstone bridge circuit as illustrated in FIG. 1C. The output or the voltage developed across the bridge circuit when a combustible gas is present provides a measure of the concentration of the combustible gas. The characteristics of compensating pelement 50 are typically matched as closely as possible with active or sensing pelement 40. In a number of systems, compensating pelement 50 may, however, either carry no catalyst or carry an inactivated or poisoned catalyst. In general, changes in properties of compensating elements caused by changing ambient conditions are used to adjust or compensate for similar changes in the sensing element.

Catalytic combustible gas sensors are typically used for long periods of time over which deterioration of the sensing element or the like and malfunction of circuits may occur. A foreign material or contaminant such as an inhibiting material or a poisoning material (that is, a material which inhibits or poisons the catalyst of the sensing element) may, for example, be introduced to the sensing element. An inhibiting material typically will "burn off" over time, but a poisoning material permanently destroys catalytic activity of the sensing element. Inhibiting materials and poisoning materials are sometimes referred to herein collectively as "poisons" or "poisoning material." In general, it is difficult to determine such an abnormal operational state or status of a combustible gas sensor without knowingly applying a test gas to the combustible gas sensor. In many cases, a detectible concentration of a combustible gas analyte in the ambient environment is a rare occurrence. Testing of the operational status of a combustible gas sensor typically includes the application of a test gas (for example, a gas including a known concentration of the analyte or a simulant thereof to which the combustible gas sensor is similarly responsive) to the sensor. Periodic testing using a combustible gas may, however, be difficult, time consuming and expensive.

For decades, combustible gas sensor designers have been perplexed with the problems of contamination and/or degradation of their catalyst structures. Sulfur-containing compounds (inhibitors) have been known to target and inhibit the catalyst structures. Filtering techniques are generally used to prevent their passage into the structure. If they do enter the structure, they are bound until a sufficient level of heat is applied to promote their release or decomposition. Volatile silicon/organosilicon compounds (poisons) are also known to cause significant issues with catalytic structures as they are permanently retained, and eventually result in the total inactivity of the catalyst. Further, high levels of hydrocarbons can also deposit incomplete and/or secondary byproducts such as carbon within the structure. Lead compounds, organophosphates and halogenated hydrocarbons are also known to poison/inhibit catalysts used in combustible gas sensors.

Manufacturers may add a layer of inhibitor/poison absorbing material outside of the supported catalyst of a sensing element as well as a compensating element. However, exposure to a sufficient amount of inhibitor/poison can still render the catalyst inactive. Moreover, increasing the mass of the sensing/compensating element increases the power requirements of the sensor, which may be undesirable, particularly in the case of a portable or other combustible gas sensor in which battery power is used.

Moreover, an inhibited or poisoned sensing element may go undetected by, for example, high sensitivity bridge and other circuits used in combustible gas sensors. Users have long reported cases where their catalytic sensors are reading zero (that is, the bridge circuitry is balanced), yet the sensors show little response to gas challenges. A notable example of this effect occurs when an organosilicon vapor such as hexamethyldisiloxane (HMDS) is introduced to the sensor. The HMDS will indiscriminately diffuse into the sensor housing and surroundings, adsorb onto the surface of the detector and/or compensator, and oxidize into a layer of silica (silicon dioxide or $SiO_2$). Since both elements are typically operated at similar temperatures, silicone deposition occurs at an equal rate, keeping the bridge in balance. Unfortunately, this renders the elements permanently inactive. Indeed, some manufacturers use this poisoning process to manufacture compensating elements or compensators for combustible gas sensors.

A number of methods and systems have been developed to sense inhibition/poisoning in a catalytic sensing element with only limited success. Recent advancements include, for example, methods utilizing additional or alternative electrical properties of the catalytic structure such as reactance to analyze one or more variables related to reactance. While such systems and methodologies are able to diagnose the deposition of poisons and inhibitors within the structure of an element for a combustible gas sensor, such systems and methodologies find limited success in detecting the deposition or formation of surface materials which can also block the sensing elements ability to interact with the target gas. It remains desirable to develop diagnostic systems and methods for catalytic sensors and structures to detect inhibition/poisoning.

SUMMARY

In one aspect, a combustible gas sensor for detecting an analyte gas includes a first element. The first element includes a first electric heating element, a first support structure on the first electric heating element and a first catalyst supported on the first support structure. The combustible gas sensor further includes electronic circuitry in electrical connection with the first element. The electronic circuitry is configured to operate in a first mode in which the first element is operated at a first temperature at which the first catalyst catalyzes combustion of the analyte gas, and in a second mode wherein the first element is operated at a second temperature which is below the temperature at which the first catalyst catalyzed combustion of the analyte gas but at which Joule heating of the first element occurs. The electronic circuitry is further configured to measure a variable in the second mode related to a mass of the first element, wherein a change in the variable is relatable to (or defined as an indication of) poisoning or inhibiting of the catalyst of the first element and the operational status of the combustible gas sensor. In that regard, one or more thresholds may be established for change in response which are predetermined to indicate if a change in mass of an element has occurred. A response in which one or more of such thresholds is exceeded may be predefined to indicate poisoning/inhibition has occurred.

The combustible gas sensor may further include a second element including a second electric heating element and a second support structure on the second electric heating element. The electronic circuitry may be in electrical connection with the second element and be configured to operate the second element at a third temperature which is lower than the temperature at which the first catalyst catalyzes combustion of the analyte gas in the first mode, and to operate the second element at a fourth temperature which is lower than the temperature at which the first catalyst catalyzes combustion of the analyte gas in the second mode. The electronic circuitry may further be configured to operate the second element to compensate for ambient conditions in the first mode and in the second mode.

In a number of embodiments, the second temperature, the third temperature and the fourth temperature are below a temperature at which one or more predetermined catalyst inhibiting compositions or catalyst poisoning compositions are oxidized on the first support structure and the second support structure. In a number of embodiments, the fourth temperature is below the temperature at which the first catalyst catalyzed combustion of the analyte gas but above a temperature at which Joule heating of the second element occurs. The second temperature, the third temperature and the fourth temperature may, for example, be below 150° C. or below 90° C. In a number of embodiments, the second temperature is within 5% of the fourth temperature or within 2% of the fourth temperature.

In a number of embodiments, the variable is selected from the group consisting of voltage, current or resistance. In a number of embodiments, the variable is resistance.

The first support structure and the second support structure may, for example, include, independently a porous, electrically insulating material. The support structures may, for example, include a porous refractory material.

The combustible gas sensor may further include a control system in communicative connection with the electronic circuitry. In a number of embodiments, the control system is configured to alter an output of the combustible gas sensor based on the change in the measured variable. In a number of embodiments, the control system is configured to provide information to a user regarding the operational status of at least the first element based on a change in the measured variable. The control system may also be configured to increase the temperature of the first element upon the change in the measured variable to attempt to burn off the foreign material.

In a number of embodiments, the second element further includes a second catalyst supported on the second support structure and the electronic circuitry is further configured to operate in a third mode in which the second element is operated at a fifth temperature at which the second catalyst catalyzes combustion of the analyte gas and in a fourth mode wherein the second element is operated at a sixth temperature which is below the temperature at which the second catalyst catalyzes combustion of the analyte gas and below a temperature at which the one or more predetermined catalyst inhibiting compositions or catalyst poisoning compositions are oxidized on the second support structure, but at which Joule heating of the second element occurs. The electronic circuitry may be further configured to measure a second variable in the third mode related to a mass of the second element, wherein a change in the second variable is relatable to poisoning or inhibiting of the catalyst of the second element.

The electronic circuitry may, for example, be further configured to operate the first element at a seventh temperature which is lower than the temperature at which the first catalyst catalyzes combustion of the analyte gas and below the temperature at which the one or more predetermined catalyst inhibiting compositions or catalyst poisoning compositions are oxidized on the first support structure in the third mode, and to operate the first element at an eighth temperature which is lower than the temperature at which the first catalyst catalyzes combustion of the analyte gas in the fourth mode, but at which Joule heating of the first element occurs. The electronic circuitry may be further configured to operate the first element to compensate for ambient conditions in the third mode and in the fourth mode.

In another aspect, a method of operating a combustible gas sensor for detecting an analyte gas, the combustible gas sensor including a first element, the first element including a first electric heating element, a first support structure on the first electric heating element and a first catalyst supported on the first support structure, and electronic circuitry in electrical connection with the first element, the method comprising: operating the electronic circuitry in a first mode in which the first element is operated at first temperature at which the first catalyst catalyzes combustion of the analyte gas, operating the electronic circuitry in a second mode wherein the first element is operated at a second temperature which is below the temperature at which the first catalyst catalyzed combustion of the analyte gas but at which Joule heating of the first element occurs, and measuring a variable via the electronic circuitry in the second mode related to a mass of the first element, wherein a change in the variable is relatable to poisoning or inhibiting of the catalyst of the first element.

In a number of embodiments, the combustible gas sensor further includes a second element including a second electric heating element and a second support structure on the second electric heating element. The method may further include operating the second element at a third temperature which is lower than the temperature at which the first catalyst catalyzes combustion of the analyte gas in the first mode via the electronic circuitry, and operating the second element at a fourth temperature which is lower than the temperature at which the first catalyst catalyzes combustion of the analyte gas in the second mode via the electronic circuitry. The electronic circuitry may, for example, operate the second element to compensate for ambient conditions in the first mode and in the second mode.

In a number of embodiments, the second temperature, the third temperature and the fourth temperature are below a temperature at which catalyst inhibiting compositions or catalyst poisoning compositions are oxidized on the support structure. The fourth temperature may, for example, be below the temperature at which the first catalyst catalyzed combustion of the analyte gas but above a temperature at which Joule heating of the second element occurs. In a number of embodiments, the second temperature, the third temperature and the fourth temperature are below 150° C. or below 90° C. The second temperature may, for example, be within 5% of the fourth temperature or within 2% of the fourth temperature.

In a further aspect, a combustible gas sensor for detecting an analyte gas includes a first element. The first element includes a first electric heating element, a first support structure on the first electric heating element and a first a catalyst supported on the first support structure, and a second element including a second electric heating element and a second support structure on the second electric heating element. The combustible gas sensor further includes electronic circuitry in electrical connection with the first element and the second element. The electronic circuitry is configured to operate in a first mode in which the first element is operated at a first temperature at which the first catalyst catalyzes combustion of the analyte gas and in a second mode wherein the first element is operated at a second temperature which is below the temperature at which the first catalyst catalyzed combustion of the analyte gas but at which Joule heating of the first element occurs. The electronic circuitry is further configured to operate the second element to compensate for ambient conditions in the first mode and in the second mode and to measure a variable in the second mode related to a mass of the first element. A change in the variable is relatable to poisoning or inhibiting of the catalyst of the first element. The second element is operated below a temperature at which one or more predetermined catalyst inhibiting compositions or catalyst poisoning compositions are oxidized on the second support structure in the first mode and in the second mode. The second temperature and the temperature at which the second element is operated may, for example, be below 150° C. or below 90° C.

The present devices, systems, and methods, along with the attributes and attendant advantages thereof, will best be appreciated and understood in view of the following detailed description taken in conjunction with the accompanying drawings.

BRIEF DESCRIPTION OF THE DRAWINGS

FIG. 5 illustrates a light-off curve for hexamethyldisiloxane (HMDS).

FIG. 7 illustrates the response to application of 15 ppm HMDS of the electronic circuitry of FIG. 6A in a first or gas detection mode and in a second or compare mode.

DETAILED DESCRIPTION

Figure 1B:
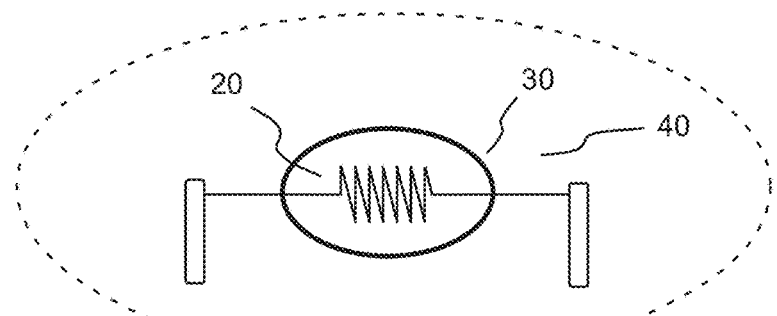
FIG. 1B illustrates an enlarged view of the active sensing element, pelement or detector of the combustible gas sensor of FIG. 1A.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etcetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a sensing element" includes a plurality of such sensing element and equivalents thereof known to those skilled in the art, and so forth, and reference to "the sensing element" is a reference to one or more such sensing elements and equivalents thereof known to those skilled in the art, and so forth.

The terms "electronic circuitry", "circuitry" or "circuit," as used herein includes, but is not limited to, hardware, firmware, software or combinations of each to perform a function(s) or an action(s). For example, based on a desired feature or need, a circuit may include a software controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "software," as used herein includes, but is not limited to, one or more computer readable or executable instructions that cause a computer or other electronic device to perform functions, actions, or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

In a number of embodiments hereof, devices, systems and method of determining the well-being or operational status of a catalytic structure (for example, a sensing element in a combustible gas sensor) are set forth that do not require the use or application of the analyte (or target) gas, a simulant thereof (that is, the application of a test gas is not required) or any other gas to a sensor. The catalytic structures or elements hereof generally include a heating element (typically a conductive element), an insulating support structure disposed on the heating element, and a catalyst disposed upon the support structure.

In a number of representative studies set forth herein, comparative methods or measurements are determined. One skilled in the art appreciates that a number of different variables related to or relatable to a change in thermal properties of an element (for example, a combustible gas sensing element) associated with a change in mass of the element may be used. Changes in such variables are, for example, related to or indicative of a change in mass resulting from the presence of a contaminant on the catalytic structure of a sensing element and/or to the sensitivity of a sensing element for an analyte. In a number of embodiments, changes in an electrical property such as resistance of an element is monitored. A variable such as voltage, current or resistance may, for example, be measured depending upon the manner in which the electrical circuitry of the sensor is controlled. For example, voltage or current in an electronic circuit can be measured and related to a change in resistance of an element. Alternatively, electronic circuitry of a sensor may be driven to maintain resistance of the element relatively constant and a voltage or a current may be measured.

Figure 2:
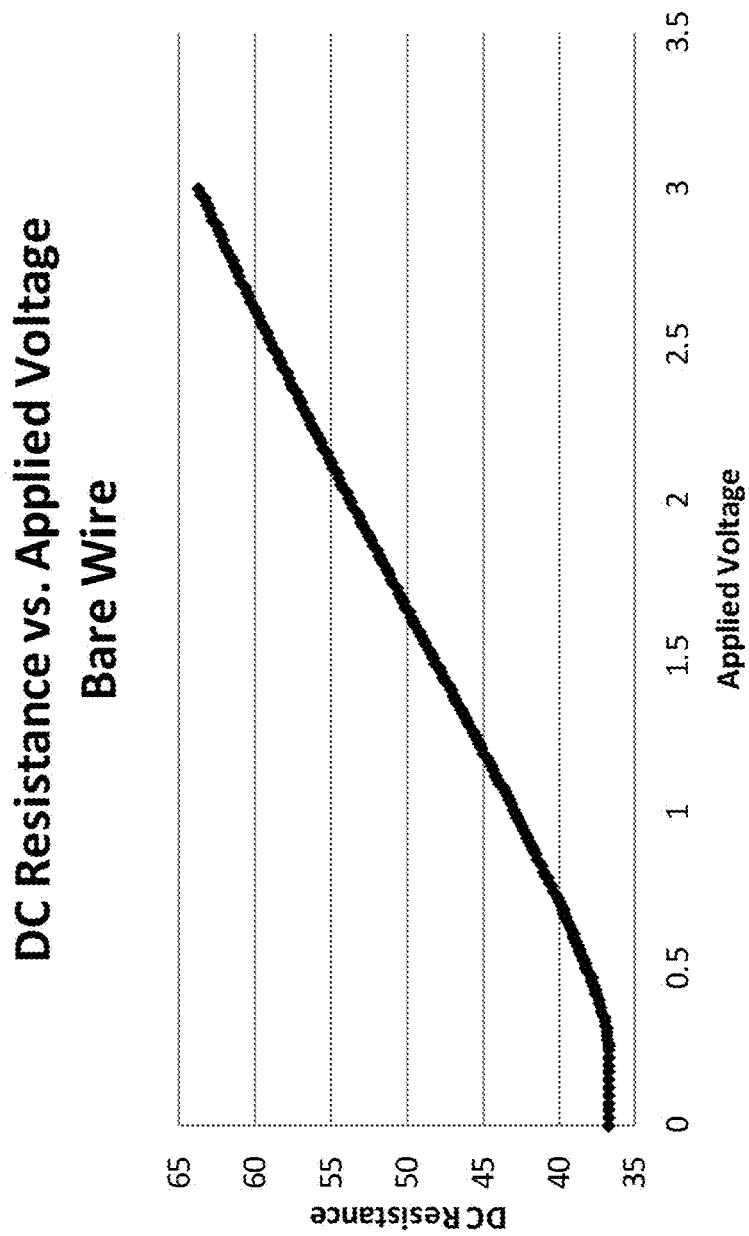
FIG. 2 illustrates an embodiment or element such as a platinum alloy heating element wire or coil and the response associated with applying a DC voltage.

FIG. 2 illustrates the response of an element such as a platinum alloy heating element wire or coil 20 associated with applying an increasing DC voltage at a fixed temperature. During the application of low voltages (0V-0.25V in the illustrated example), the element resistance remains consistent. In this voltage range, resistive changes are predominantly governed by ambient temperature fluctuations. The principles employed in this regime are well known and are used, for example, in resistive thermometers. In that regard, the platinum resistance thermometer is a versatile instrument for temperature measurement in the range from approximately −200° C. to +1000° C. One may, for example, use the simplified Callendar-Van Dusen equation to determine the temperature dependent resistance as follows:

$$R_t = R_0[1+\alpha(t-t_0)]$$

wherein $R_t$ is the resistance of the element at temperature t, $R_0$ is the resistance at a standard temperature $t_0$, and $\alpha$ is the temperature coefficient of resistance. The above principle may, for example, be used as described in U.S. Pat. No. 8,826,721, the disclosure of which is incorporated herein by reference, to operate a sensor element in a low power (voltage) mode in which the sensor element including an active catalyst is able to function as a compensating element or compensator.

Referring again to FIG. 2, the application of higher voltages (>0.5V in the representative example of FIG. 2) will cause the wire to increase in temperature, and thus in resistance. This effect is known as Joule's first law or the Joule-Lenz law. Joule heating, also known as ohmic heating or resistive heating, is the process by which the passage of an electric current through a conductor releases heat. In the case of a sensor element including a catalyst support structure, the heat transfer from the heating element/wire will eventually reach an equilibrium as the heat will conduct from the heating element to the support structure of the sensing element (including, for example, a refractory support structure and a catalyst supported thereof) and then via fluidic convection through the surrounding gases. Thermal equilibrium will remain balanced until (a) the ambient temperature changes; (b) the makeup of the surrounding gas mixture is altered, or (c) the transfer of heat between the wire and the mass of the element changes (as a result of a mass or density change). These effects are all competing and interacting effects.

In the case of a combustible gas sensor, a heating element such as heating element 20 of FIG. 1B (for example, a conductive wire, coil or surface) is used to sufficiently raise the structure of the element (including the support structure and catalyst) to a temperature to promote the catalytic reaction of the analyte or target gas. As used herein with respect to an element hereof (that is, a sensing element or a compensating element), temperature refers to an average temperature over the volume of the element. Heating elements have generally been made from coils, and over time smaller diameter wires have been used to reduce the power consumption of the element.

Figure 1A:
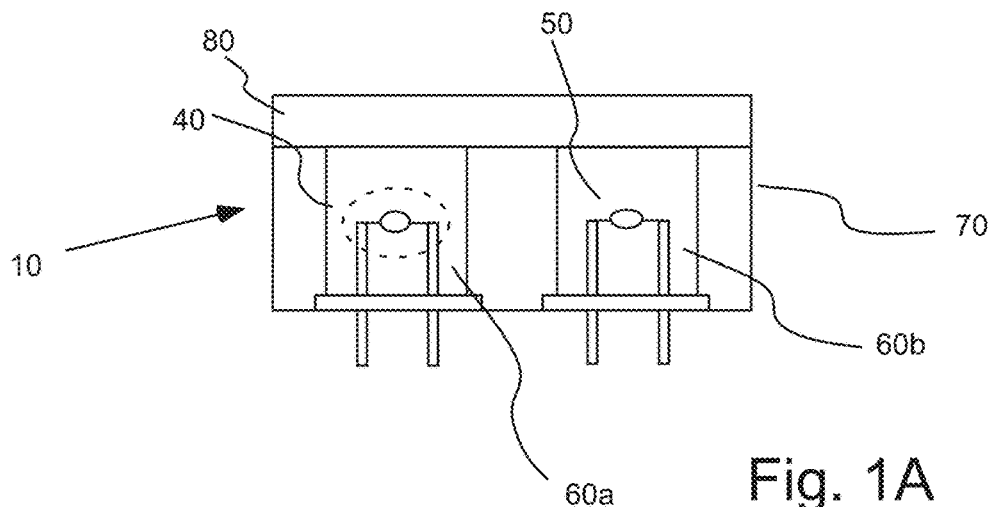
FIG. 1A illustrates an embodiment of a currently available combustible gas sensor.
Figure 1C:
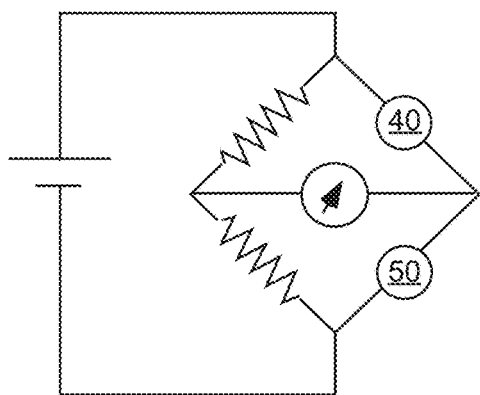
FIG. 1C illustrates an embodiment of the circuitry of the combustible gas sensor of FIG. 1A.
Figure 3A:
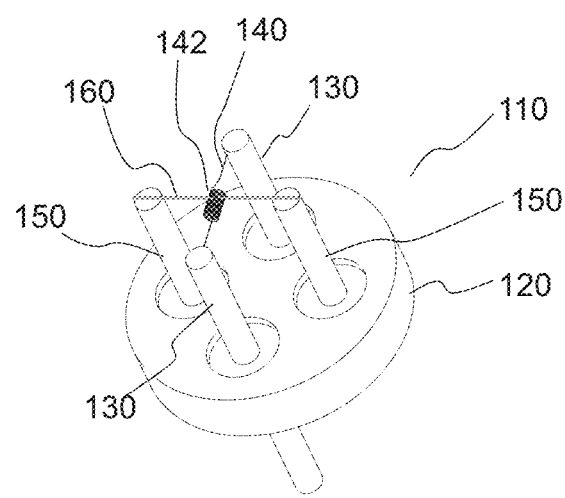
FIG. 3A illustrates a perspective view of an embodiment of a detector assembly wherein a sensing element is supported by a supporting wire.
Figure 3B:
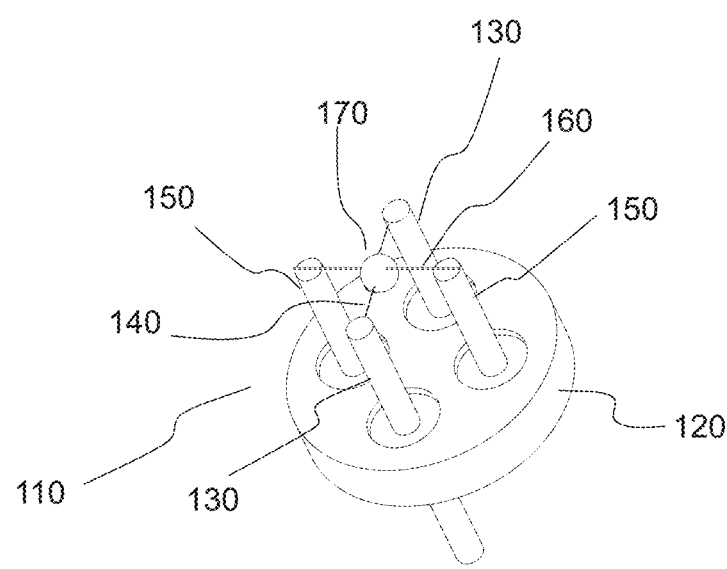
FIG. 3B illustrates a perspective view of the detector assembly of FIG. 3A including a ceramic bead (upon which a catalyst is supported) formed over the sensing element wire.
Figure 3C:
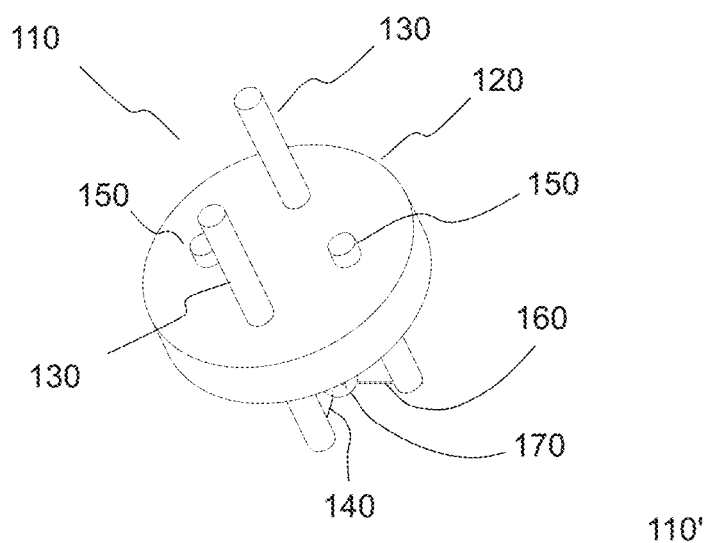
FIG. 3C illustrates another perspective view (generally opposite that of FIG. 3B) of the detector assembly of FIG. 3A.

The use of conductive elements such as wires having relatively small diameter in element for combustible gas sensors is, for example, disclosed in U.S. Pat. No. 8,826,721. In that regard, FIGS. 3A through 3C illustrate a representative embodiment of a detector/element assembly 110 which may, for example, be used in a gas sensor as illustrated in FIG. 1A. Element assembly 110 includes a base 120 to which two electrically conductive contact members 130 (extending members or posts in the illustrated embodiment) are attached. A sensing conductive element 140 is connected between contact members 130, wherein each end of conductive elements 140 is connected to or anchored to one of contact members 130. In the illustrated embodiment, conductive element 140 includes an intermediate section including a coiled section 142 that can, for example, be located approximately centrally between the ends of conductive element 140. Wires and/or other conductive elements for heating elements are selected to have a favorable temperature coefficient for sensing applications and are generally a precious metal or alloy.

Element assembly 110 further includes two support members 150 (extending members or posts in the illustrated embodiment) connected to base 120. In the illustrated embodiment, a support member or element 160 in the form of, for example, a wire, a ribbon, a rod or other suitable support structure or material extends between support members or posts 150. Base 120, contact members 130 and support members 150 can, for example, be formed of a metal such as KOVAR® (a nickel-cobalt ferrous alloy designed to be compatible with the thermal expansion characteristics of borosilicate glass) available from Carpenter Technology Corporation of Reading, Pa. Contact members 130 and support members 150 can, for example, be sealed to base 120 using a glass such as borosilicate glass to provide electrical isolation.

Using a strong yet relatively thin support element 160 anchored, connected or attached at each end thereof (for example, anchored at two support members or posts 150) prevents bead movement in all three dimensions while limiting heat loss. In the illustrated embodiment of FIGS. 3A through 3C, support element 160 passes through and contacts one of the coils of coiled section 142. Contact between support element 150 and conductive element 140 is thus minimal. As described below, support element 150 need not contact conductive element 140 to provide support therefor, but can contact or pass through a catalyst support member or structure 170 encompassing conductive element 140.

A balance may, for example, be established between the tensile strength and the thermal conductivity to achieve an effective result for support element 150. In general, a quotient or ratio calculated by dividing the tensile strength in units of pounds per square inch of psi by the thermal conductivity in units of watts/cm/° C. may, for example, be at least 250,000, at least 400,000 or even at least 500,000. For example, in several studies, a support element in the form of a wire made from an alloy of platinum and tungsten had a tensile strength of 250,000 psi and a thermal conductivity of 0.5 watts/cm/° C., resulting in a quotient of 500,000. For support elements having a higher tensile strength, a higher thermal conductivity may be acceptable since support elements of smaller average diameter (or average cross-sectional area) can be used (resulting in less mass to conduct heat away from the sensing element). Moreover, reducing the size/volume of the element reduces the effect of ambient humidity and pressure changes on the sensor. For example, in the case of a tungsten support element having a tensile strength of 600,000 psi and a thermal conductivity of 1.27 watts/cm/° C., a smaller average diameter support element can be used to achieve a similar result to that achieved with the platinum-tungsten alloy support element described above. Alternatively, one could also choose a support element of an alloy of platinum with 20% iridium having a larger average diameter. Such a platinum-iridium alloy has a tensile strength of 120,000 psi and a thermal conductivity of 0.18 watts/cm/° C. Metal support elements or metal alloy elements having the above-described properties can be used to maximize strength/support while minimizing heat loss.

In that regard, in several embodiments, support element 160 exhibits relatively high strength (for example, having a tensile strength of at least 100,000 psi, at least 250,000 psi, or even at least 400,000 psi) as well as low thermal conductivity (for example, having a thermal conductivity less than 1.5 less watts/cm/° C., less than 0.5 watts/cm/° C., no greater than 0.25 watts/cm/° C., or even no greater than 0.10 watts/cm/° C.) to provide a quotient as described above. In a number of embodiments, the average diameter of support element 160 (in the case of a support element of a generally circular cross-section) is in the range of approximately 0.0005 (12.7 µm) to 0.0025 inches (63.5 µm). In the case of support elements having a noncircular cross-section, the average cross-sectional area can, for example, be in the range of the average cross-sectional area of an element of generally circular cross-section having an average diameter in the range of approximately 0.0005 to 0.0025 inches. References herein to elements having a certain average diameter are also references to elements having a generally noncircular cross-section, but having an average cross-sectional area equivalent to the average cross-sectional area provided by the stated average diameter. In several representative studies, an in-molded wire was used as support element 160. In several such embodiments, a platinum-tungsten alloy support element 160 having an average diameter of approximately (that is, within 10% of) 0.001 inches (63.5 µm) provided a robust support, and did not result in measurable additional power required to operate sensing element 140. Alloys of tungsten, nickel, molybdenum or titanium with, for example, platinum, palladium or rhodium can, for example, be used in support element 160.

As illustrated in FIG. 3B, catalyst support structure 170 (for example, a ceramic bead in a number of embodiments) can be formed on coil section 120 of sensing conductive element 140 to support a catalyst and form a sensing element/pelement. In forming catalyst support structure 170 as a refractory material such as a ceramic bead, an aluminum oxide suspension may, for example, be fired onto coiled section 142. The resultant catalyst support structure/ceramic bead 170 may be impregnated with a catalyst. Although a bare wire comprising a catalytic material (such as platinum) can be used as a sensing element in certain embodiments of a combustible gas sensor, a catalyst support structure 170 (such as a ceramic bead) provides increased surface area for one or more catalyst species.

In the embodiment illustrated in FIGS. 3A through 3C, catalyst support structure 170 is formed over (to encompass) conductive element 140 and support element 160. In a number of embodiment, support element 160 need not contact conductive element 140 to provide support therefor. For example, support element 160 can pass through or contact catalyst support structure 170 without contacting conductive element 140 and indirectly provide support for conductive element 140. To provide support for conductive element 140 in three dimensions, support element 160 preferably passes through catalyst support structure 170.

The support assembly, including, for example, support member 150 and support element 160, enables the use of a sensing element 140 having a relatively small average diameter. For example, a wiring having an average diameter no greater than approximately 20 µm of 10 µm may be used. Such a small average diameter wire (with a corresponding higher per unit length resistance than larger diameter wires) lends itself well to reducing the required operating current (which is very desirable in portable applications), and thus the required power levels.

In a number of embodiments, the support members or catalyst support members hereof have a volume less than a sphere having a diameter of 500 µm (wherein the volume of a sphere is calculated by the formula $4/3 \times \pi \times (D/2)^3$, that is, less than $6.5 \times 10^7$ µm$^3$). The first catalyst support member can have a volume no greater than a sphere having a diameter of no greater than 440 µm (that is, less than $4.46 \times 10^7$ µm$^3$), or a diameter no greater than 300 µm (that is, less than $1.4 \times 10^7$ µm$^3$).

Figure 3D:
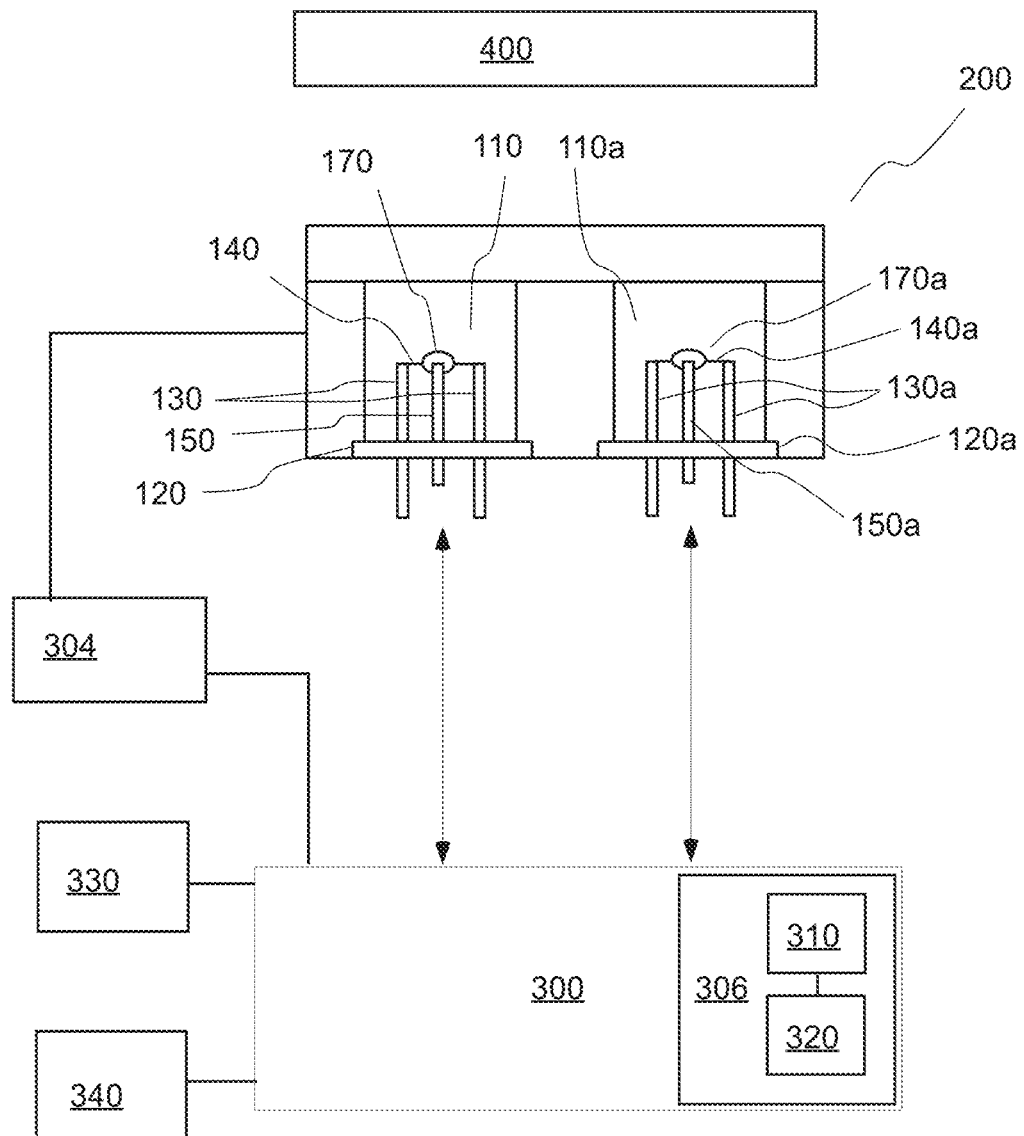
FIG. 3D illustrates a combustible gas sensor including two detector assemblies of FIG. 3B in electrical connection with control and measurement circuitry (illustrated schematically).

A sensor or sensor assembly 200 as illustrated in FIG. 3D may be made which includes two element/detector assemblies 110 (first element) and 110a (second element; in FIG. 3D, elements of second element 110a are numbered similarly to like elements of first element 110, with addition of the designation "a" thereto). Electronic circuitry 300 may be placed in electrical connection with contact posts 130 and 130a of each of element assemblies 110. In the case of a sensor fixed at a position within a facility, power may be provided from a remote source. As described above, in the case of a portable sensor, power source 304 may include one or more batteries. As also described above, the sensor system may also include a control system 306 which may, for example, include control circuitry and/or one or more processors 310 (for example, a microprocessor) and an associated memory system 320 in communicative connection with processor(s) 310.

Figure 4:
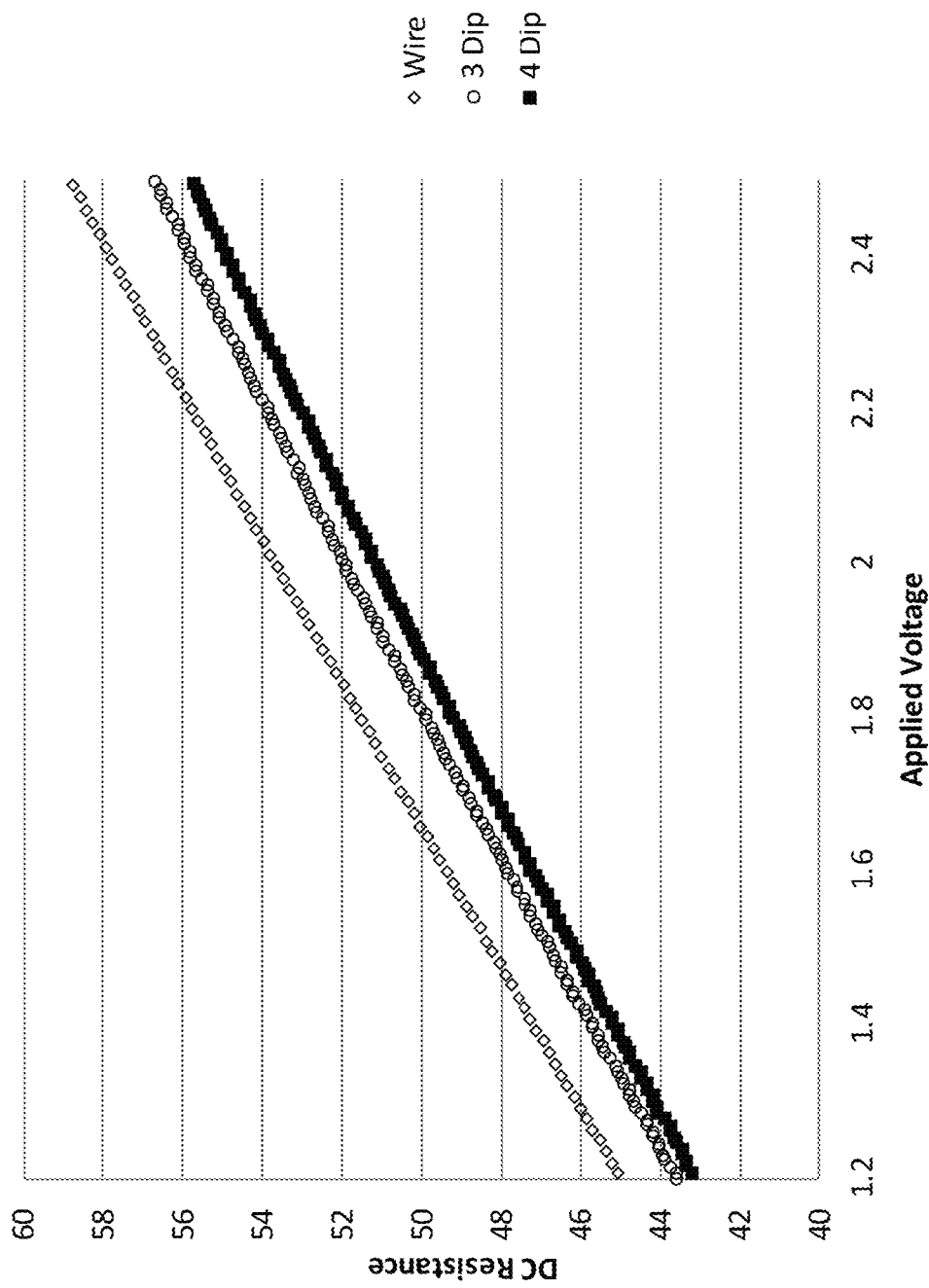
FIG. 4 illustrates the effects of mass loading of refractory materials onto a platinum alloy heating element wire or coil and the response associated with applying a DC voltage.

FIG. 4 illustrates the effects of mass loading on the resistance of a heating element/wire. In that regard, FIG. 4 shows the difference between a bare coiled wire, a coil wire after formation thereon of a refractory support via the application of three dips of a solution of a precursor for a refractory material, and a coil wire after thereon of a refractory support via the application of four dips of refractory materials. As known in the art, a heating element in the form of a wire or wire coil be dipped it into an aqueous solution of a precursor of a refractory. The precursor may then be converted into the refractory material by heating (for example, by the passage of an electrical heating current through the heating element). The dipping process is usually repeated to build up a support structure of the desired size/average diameter around the heating element. A solution or dispersion of a catalyst may then be applied to the outer surface of the support structure. As the mass of the support structure is increased (via increasing the number of dip within precursor material), the heating element (wire or coil) resistance decreases as a function of mass for any given applied voltage (that is, any line drawn parallel to the Y axis in FIG. 4). Mass loading as a result of deposition of an inhibitor or a poison on the support structure also results in a decrease in resistance.

As described above, the operation of a catalytic combustible gas sensor may proceed through electrical detection of the heat of reaction of a combustible gas on the oxidation catalyst (for example, through a resistance change via a Wheatstone bridge). The oxidation catalysts may, for example, operate in the temperature range of 350-600° C. for methane detection. Among common hydrocarbons, methane requires the highest temperature for combustion, hydrogen requires low temperatures, and larger alkanes fall in between, with longer to shorter carbon chain requiring lower to higher light-off temperatures.

The active or sensing element in a number of combustible gas sensors hereof may, for example, be operated at a generally constant voltage, a constant current or a constant resistance (and thereby at a constant temperature) during a particular mode of operation. In a number of embodiments of combustible gas sensors hereof, the electronic circuitry of the combustible gas sensor operates in a first mode in which a first or sensing element is heated to or operated at a temperature at which the first catalyst catalyzes combustion of the analyte gas (for example, above 300° C. for methane). In a second mode, the electronic circuitry operates to heat the sensing element to a second temperature which is lower than the first temperature. The second temperature is below the temperature at which the first catalyst catalyzes combustion of the analyte gas but is at or above a temperature at which Joule heating of the first element occurs. The second temperature may also be below the light off temperature of other combustible gasses that may be in the environment being tested by the sensor. The second temperature is also typically lower than a temperature at which one or more inhibitors and/or poisons which may be predetermined (for example, inhibitor(s) or poison(s) that may be present in the ambient environment) are deposited/oxidized upon or within the support structure of the first element. Once again, however, the second temperature is at or above the temperature at which Joule heating occurs (see the sloped portion of FIG. 2, for example) so that changes in mass affect the resistance thereof (see FIG. 4, for example).

The electronic circuitry measures a variable in the second mode related to a mass of the first element. The variable is measured over time (that is, through multiple cycles between the first mode and the second mode), and change in the variable over time is analyzed to relate the change in the variable to a change in mass of the first element. The change in mass is an indication of deposition of a poison or inhibitor of the catalyst of the first element. For example, voltage, current or resistance of the second element can be measured (depending upon the manner in which the system is driven to control voltage, current and/or resistance in the second mode).

As described above, the first element will react to changes in various ambient conditions that can change its output in the first mode and/or the second mode (that is, anything that changes the energy balance on the first element). Changes in ambient conditions over time may thereby create errors measurements by the electronic circuitry in the first and/or the second mode or operation. Changes in ambient conditions that effect measurements include changes in ambient temperature, humidity, and/or pressure.

Reducing the size/mass of the sensing element may reduce the effects of such ambient phenomena. In a number of embodiments, however, compensation may be made for changes in ambient conditions in measurements made by the electronic circuitry. One or more such ambient conditions may be measured and one or more algorithms executed to correct measurements by the electronic circuitry. A second or compensating element may also be used to effectively compensate for changes in ambient conditions.

In a number of embodiments, during the first mode of operation as described above, a second or compensating element is operated at a third temperature which is lower than the temperature at which the first catalyst catalyzes combustion of the analyte gas (that, is at a temperature at which the catalyst is substantially or completely inactive to catalyze combustion of the analyte gas). The third temperature may also be below the light off temperature of other combustible gasses that may be in the environment being tested by the sensor. The third temperature may also be lower than a temperature at which one or more inhibitors and/or poisons may be deposited/oxidized upon or within the support structure of the second element (that is, below a temperature at which mass would be added to the second element in the presence of such inhibitors and/or poisons). The third temperature may, for example, be ambient temperature or another temperature associated with a power input below which resistance change/Joule heating occurs in the second element. The second element may, for example, include no catalyst on the support structure thereof, an inactive/poisoned catalyst on the support structure thereof, include no catalyst but having a poison deposited thereon, or an active catalyst on the support structure thereof. In a number of embodiments, the second element is closely matched in structure to the first element as known in the art. In the first mode, the first element operates as a sensing element and the second element operates as a compensating element.

In the second mode as described above, the second element is operated at a fourth temperature which is lower than the temperature at which the first catalyst catalyzes combustion of the analyte gas. The fourth temperature is also lower than a temperature at which inhibitors and/or poisons are deposited/oxidized upon or within the support structure of the first element. The fourth temperature may, for example, be ambient temperature or another temperature associated with a power input below which resistance change/Joule heating occurs in the second element. In a number of embodiments, the fourth temperature is a temperature at which Joule heating of the second element occurs. In a number of embodiments, the second temperature and the fourth temperature are equal or substantially equal (that is, differing by no more than 5%, no more than 2% or nor more than 1%). By having the second temperature and the fourth temperature be equal or substantially equal, effects of ambient temperature changes, relatively humidity changes, etc. may be reduced or minimized in measurements hereof, and compensation is simplified. The electronic circuitry is adapted to or operable to measure a variable in the second mode related to a mass of the first element.

In a number of embodiments, while an element hereof is operated as a compensating or compensator element, the operating temperature of that element does not exceed a temperature at which a poison or an inhibitor is deposited/oxidized upon the element. When a compensating element is heated above the temperature at which a poison or an inhibitor is deposited/oxidized upon the element in a sensor system, and particularly if the compensating element is heated to approximately the operating temperature of the sensing element (that is, a temperature at which catalytic combustion of an analyte occurs), both elements may be poisoned or inhibited. If both elements are poisoned or inhibited, the elements yield little measurable difference in output.

In general, poisons and/or inhibitors are oxidized on the surface of an element (for example, on a support structure of the element) at a certain minimum temperature, sometimes referred to as "light-off" temperature. HMDS is a common poison and has a relatively low light-off temperatures. A light-off curve for HMDS is illustrated in FIG. 5, demonstrating a light-off temperature of greater than 150° C. In a number of embodiments, the third and fourth temperatures of the second element or other element hereof, when operated as a compensator element is less than 150° C. or less than 90° C. In a number of embodiments, the third temperature is approximately ambient temperature. In a number of embodiments, the second temperature of the first element or other element hereof, when operated in the second mode to test for mass change is less than 150° C. or less than 90° C.

Figure 6A:
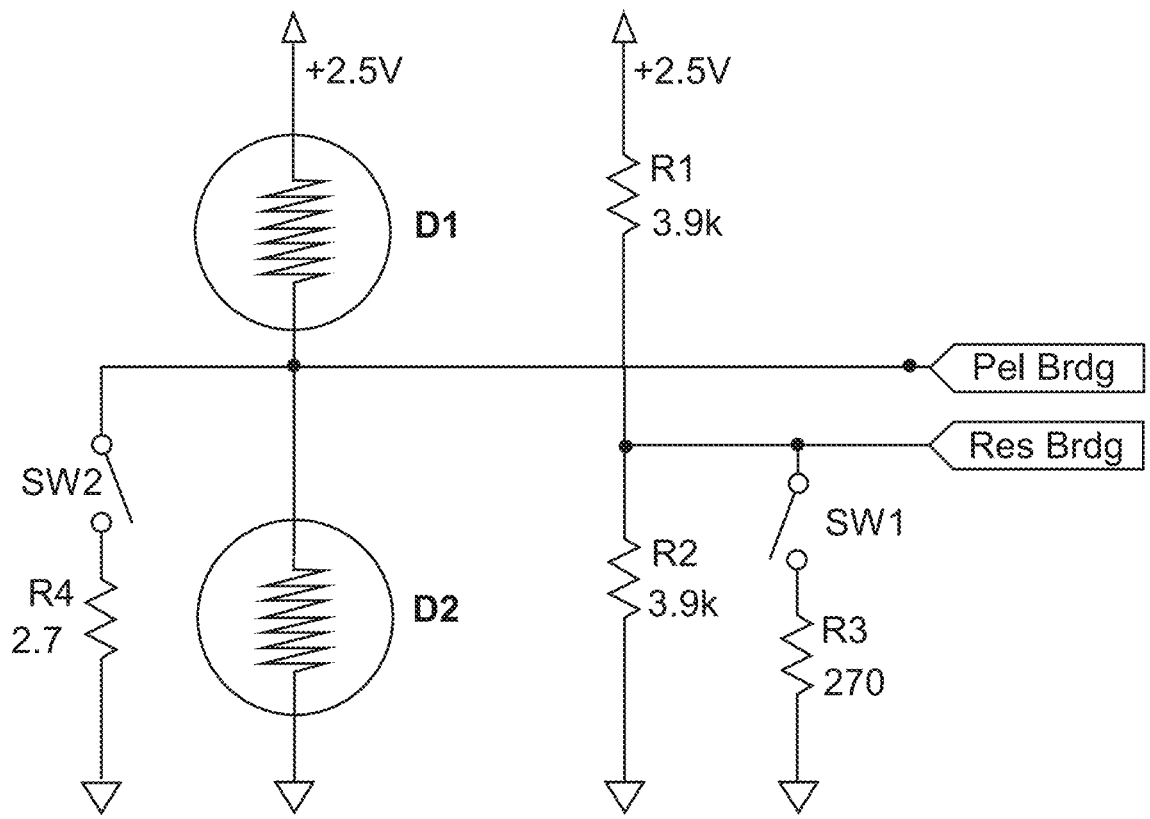
FIG. 6A illustrates a representative circuit diagram of an embodiment of electronic circuitry for use herein in which elements are connected within a bridge circuit.

FIG. 6A illustrates an embodiment of electronic circuitry to enable operation in the first mode and second mode as described above for the evaluation of mass loading on a sensing element, while generally excluding the effects of ambient temperature and the makeup of the surrounding gas mixture. Once again, the mass loading may take the form of poisons or inhibitors attaching to/depositing upon the sensing structure, either internally or on the surface.

In the circuit configuration of FIG. 6A, first element or detector D1 acts as a classical sensing element, and a second element or detector D2 acts as a compensator element. When switches SW1 and SW2 are closed, the bridge circuit operates much like a standard pellistor configuration. In this configuration, there is approximately 100 mV across the compensating element D2 and 2.4V across the sensing element D1. This mode is referred to as the first mode, as described above, or the "gas detection mode." When switches SW1 and SW2 are open, the bridge circuit is operated in the second mode, as described above, or the "comparison mode." In the second or comparison mode, there is approximately 1.25V across each element D1 and D2, which is compared against the two 3.9 kΩ resistors. These two outputs may, for example, be run to a differential amplifier to examine the differences in voltage across the bridge circuit.

In the circuit configuration of FIG. 6A, with switches SW1 and SW2 closed, second element D2 acts as an unheated compensating element. Operating at ambient temperatures (or other temperature below which inhibitors/poisons attached/deposit) prevents second element D2 from being catalytically active (even if an active catalyst is supported thereon) and from poisoned or inhibited as described above. First element D1 functions as a high-temperature sensing element, which exposes first element D1 to poisoning or inhibiting of the catalyst thereof. When switches SW1 and SW2 are opened and the circuit is in second or compare mode, the first and second elements D1 and D2 will reach a thermal equilibrium related to their respective masses. While in compare mode, each of first element D1 and second element D2, may be operated at equal or substantially equal temperature (that is, at a temperature in the Joule heating range) in the embodiment of FIG. 6A, and will thus respond in an equal or substantially equal manner to ambient conditions. If the mass of the active/sensing first element D1 has increased, it will have a lower resistance as compared to previous interrogations, thus creating a change in the bridge balance.

The comparison evaluation may be performed at any applied voltage. The circuit diagram of FIG. 6A uses 1.25V for the simplicity of explaining the concept. One may also use a variety of pulsed, modulated or switched operations to make the comparison.

In the case that second element D2 includes a supported active catalyst, the functions of second element D2 and first element D1 may be switched or cycled so that first element D1 becomes the (high-power/high temperature) sensing element and second element D2 becomes the (low power/low temperature) compensating element. Electronic circuitry 300 (see FIG. 3D), may, for example, effect automatic, periodic switching between sensing element modes as well as periodically switch the function of first element D1 and second element D2. Alternatively or additionally, switching between modes and/or between sensing element functionality can be effected after a manually initiated or controlled event such as a power off/power on (or power cycling) procedure or event. Prior to completion of a switch of the function of first element D1 and second element D2, a comparison mode test may be carried out to ensure that there has been no poisoning of the element that has most recently been operated in the high-power, high-temperature sensing mode. A plurality of sensing elements (for example, three or more) may be used to improve the reliability and ensure the sensors remains on-line for its intended safety purpose. In a number of embodiments hereof, one or more sacrificial or scavenger elements 400 (illustrated schematically in FIG. 3D) can be provided (for example, a heated support structure) having only the function of collecting inhibitors and poisons. Likewise, filters can be provided to filter contaminants such as sulfur, either spaced from an element or on an element.

In a number of embodiments, the second mode as described above is initiated in the interim period between switching the functions of elements such as first element D1 and second element D2. In the case that D1 has most recently been operated in the high power/high temperature mode (that is, at the first temperature as described herein) for catalytic oxidation of the analyte, the temperature of D1 may be decreased to the second temperature as described herein (that is, to a temperature below the temperature at which the analyte is catalytically combusted, but above a temperature at which joule heating occurs). The temperature of D2 is adjusted from the third temperature as described herein to the fourth temperature as described herein (that is, to a temperature below the temperature at which the analyte is catalytically combusted, but above a temperature at which joule heating occurs). Once again, the electronic circuitry hereof measures a variable in the second mode related to a mass of first element D1. The variable is measured over multiple occurrences of the second mode and change in the variable over time is analyzed to relate the change in the variable to a mass change associated poisoning or inhibiting of the catalyst of first element D1.

Once the measurement(s) of the second mode is/are completed, the temperature of first element D1 may be further decreased to a fifth temperature (which may be below the temperature at which joule heating occurs) so that first element D1 may be operated as a compensating element in a third mode, which is a measuring mode in which the second element D2 functions as a sensing element. Subsequently, in a fourth mode or comparison mode, the temperature of first element D1 may be increased to a sixth temperature (which, as described above, may be above the temperature at which joule heating occurs). Alternatively, the fifth and sixth temperatures may, for example, be ambient temperature or another temperature associated with a power input below which resistance change/Joule heating occurs in the second element. In the third mode, the temperature of second element D2 is increased to a seventh temperature which is above the temperature at which the second catalyst of second element D2 catalyzes combustion of the analyte gas. In the fourth mode, the temperature of second element D2 is decreased to an eighth temperature which is below the temperature at which the second catalyst of second element D2 catalyzes combustion of the analyte gas but above the temperature at which joule heating occurs. The electronic circuitry hereof measures a variable in the fourth mode related to a mass of second element D1. The variable is measured over multiple occurrences of the fourth mode and change in the variable over time is analyzed to relate the change in the variable to a mass change associated poisoning or inhibiting of the catalyst of second element D2. In a number of embodiments, a sensor hereof is repeatedly cycled through the modes described above.

Figure 6B:
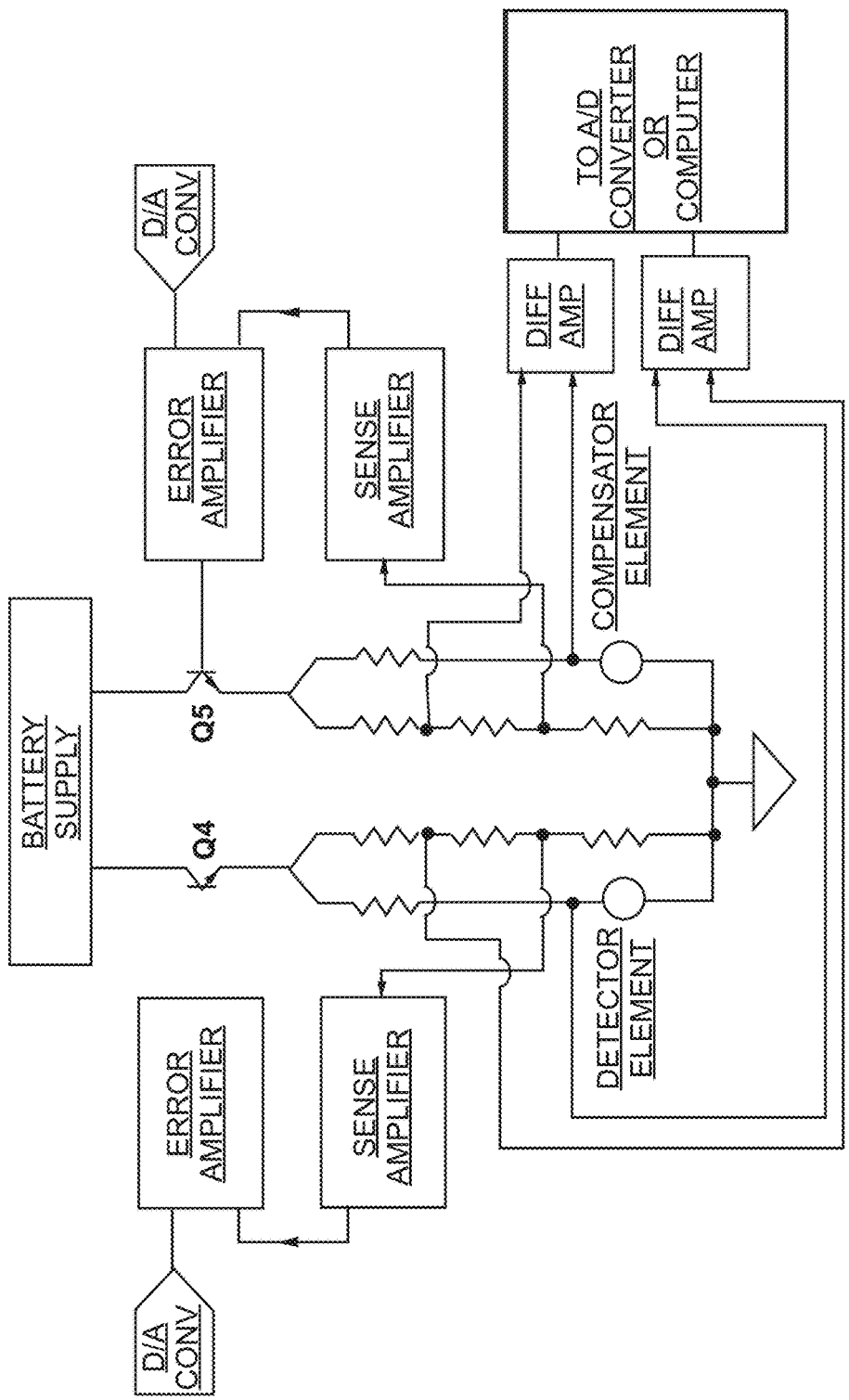
FIG. 6B illustrates another embodiment of electronic circuitry hereof for independent control of multiple elements (that is, sensing elements and compensating elements).

Various electronic circuits and/or control methodologies may be used in the devices, systems and/or methods hereof. As, for example, disclosed in U.S. Pat. Nos. 8,826,721 and 5,780,715, the disclosures of which are incorporated herein by reference, elements or detectors may operate independently (see FIG. 6B for a representative example). As described in, for example, U.S. Pat. No. 5,780,715, FIG. 6B illustrates an embodiment of separate control of detectors/elements in simplified block form. In the illustrated embodiment, the electronic circuit includes two controlled current source circuits, enabled by transistors Q4 and Q5, respectively. Each of transistors Q4 and Q5 may, for example, be a bipolar transistor, a junction field effect transistor, a metal-semiconductor field effect transistor, or a metal-oxide semiconductor field effect transistor. One current source Q4 passes current from the power/battery supply(ies) through the resistive sensor or detector element which is used to detect a combustible gas analyte as describe herein. The other current source Q5 passes current from power/battery supply(ies) through the resistive reference or compensating sensor or element. Current sources Q4 and Q5 may, for example, be controlled by a conventional programmable digital to analog converter (DAC), which may, for example, set the voltage levels at the bases of the enabling transistors Q4 and Q5 to control the amount of current flowing from the power/battery supply(ies) through detector/compensator elements, respectively. In the absence of the combustible gas analyte to be detected, the current through the detector element may be regulated to equal the current through the compensator element. Alternately, the circuitry can be arranged in a controlled voltage source configuration in which a constant identical voltage is ideally maintained across the sensor element and the compensator element.

FIG. 7 illustrates the result of testing a 450 µm diameter catalytic structure using the electronic circuitry of FIG. 6A. Each data point represents data recorded after each 30 second exposure to 15 ppm HMDS. During this recording period, a measurement is taken in both first/gas detection and second/compare modes. The gas detection mode signal is used to calculate the amount of Span Loss (signal) as compared to the start of the experiment. The compare mode signal is used to calculate the bridge shift as a result of the mass increase on the sensing element or detector. As illustrated in FIG. 7, there is a correlation between the measurements.

Figure 8:
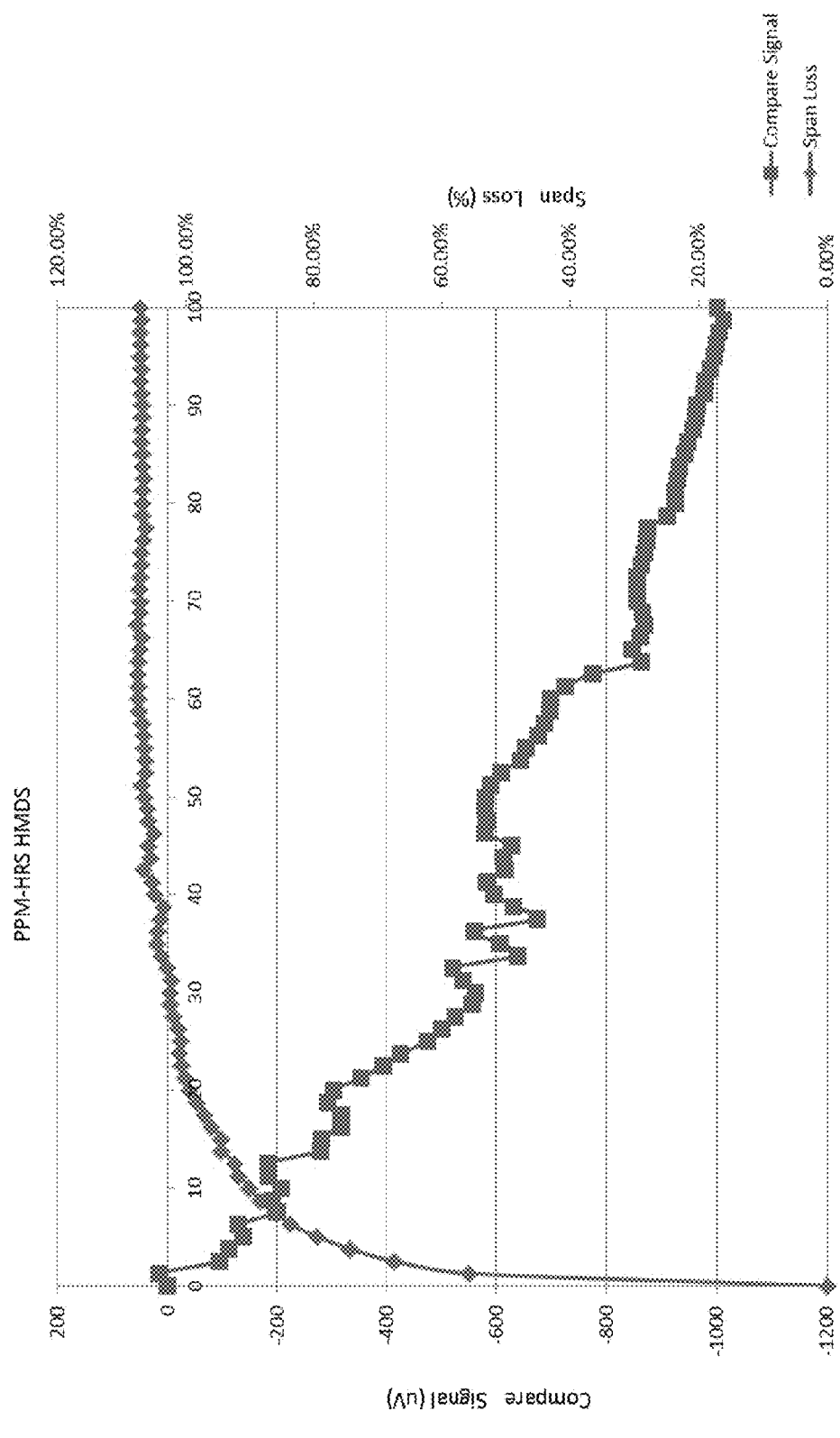
FIG. 8 illustrates the response to long term application of 15 ppm HMDS of the electronic circuitry of FIG. 6A in the first or gas detection mode and in the second or compare mode.

To further illustrate the functionality of the devices, systems and methods hereof, FIG. 8 illustrates the result of a long term application of 15 ppm HMDS to a 450 µm diameter catalytic structure using the electronic circuitry of FIG. 6A. After 25 PPM-HRS of cumulative exposure to HMDS, the device no longer responds to the application of analyte (that is, there is 100% span loss). The second/compare mode signal, however, continues to trend downward. While the sensing element (D2) can no longer respond to the analyte, it can continue to gain mass as the HMDS continues to adhere onto the surface. Therefore, the second/compare mode signal continues to indicate the mass increase.

In analyzing element response/data hereof to determine if a contaminant such as an inhibitor or a poison has been deposited upon an element hereof (that is, if there has been a change in mass), a baseline response may first be established. The baseline response may be established when there is high confidence that the element or elements have not been contaminated. For example, a baseline response may be determined at the time of manufacture. A sensor system may subsequently be placed in a compare or interrogations mode as described above to determine if contamination has occurred. In that regard, one or more thresholds may be established for change in response to determine if poisoning/inhibition has occurred. Such interrogations may, for example, occur periodically. In a number of embodiments, the control system of the sensor system may automatically initiate such an interrogation mode on a periodic or other basis. Moreover, an interrogation mode may also be initiated manually in a number of embodiments.

As described above, element hereof may be relatively small, which reduces the effects of changes in relative humidity and/or pressure in the ambient environment upon element response. Moreover, low thermal time constants associated with low thermal mass assist in providing quick response times and reducing the time an element may be unavailable for use in a detection or gas detection mode. In a number of embodiments, the first sensing element has a thermal time constant of 8 second or less or 6 seconds or less. A sensing or other element may, for example, comprise a MEMS pellistor or a pelement of low thermal mass to provide a thermal time constant of 8 seconds or less (or 6 seconds or less). The thermal time constant of an element is defined as the time required to change 63.2% of the total difference between its initial and final temperature when subjected to a step function change in drive power, under zero power initial conditions.

As used herein, the term "MEMS pellistor" or "MEMS element" refers to a sensor component with dimensions less than 1 mm that is manufactured via microfabrication techniques. In a number of representative embodiments, sensing elements formed as MEMS pellistors hereof may be manufactured with a thick film catalyst, powered to an operating temperature by resistive heating and are used to detect combustible gases. In a number of representative embodiments, the thickness and diameter for a MEMS catalyst film is 15 microns and 650 microns, respectively.

Although certain advantages may be achieved using elements having low volume/low thermal mass as described above, the devices, systems and methods described above may also be used with elements of relative high volume/high thermal mass. For example, standard pelements, which may, for example, have an effective diameter of greater than or equal to 1 mm, may be used herein.

In several embodiments, pulse width modulation may, for example, be used to control the energy delivered to elements hereof. Pulse width modulation is a well-known control technique used to control the average power and/or energy delivered to a load. In embodiments hereof, a voltage is supplied to, for example, a pellistor element, MEMS hotplate or other heating element to heat a supported catalyst to a desired temperature. Because the elements (including, for example, pelements, pellistors and MEMS elements) hereof may have relatively low thermal mass, the cycle times can be relatively short. Low mass pelements are, for example, described in U.S. Pat. No. 8,826,721 and in U.S. patent application Ser. No. 15/343,956, the disclosure of which is incorporate herein by reference.

In pulse width modulation, heating energy (that is, heating voltage(s) or heating currents(s)) may be periodically supplied to the heating element(s) during an "ON time". Rest energy (that is, rest voltage(s) or rest current(s)), which is less than the heating energy may be supplied during a "REST time". The total of the higher-energy or ON time plus the lower-energy or REST time correspond to a cycle time or a cycle duration. Gas concentration or the analyte is measured during the ON time. The heating energy (voltages/currents) supplied during the ON time may be constant during the ON time or may be varied (for example, supplied as heating voltage/current plateau or as heating voltage/current ramp). The rest energy (voltages/currents) may be equal to zero, or be sufficiently lower than the heating energy so that the gas sensor does not consume any gas or substantially any gas to be detected. Similar to the ON time, the rest energy supplied during the REST time may be constant during all the REST time or may be varied (for example, supplied as rest voltage/current plateau or as rest voltage/current ramp). The cycle may be repeated.

An advantage to operating in pulse mode is significantly lower power consumption as compared to continuous mode. Another advantage is improved span response as a result of adsorption of excess combustible gas on the catalyst at cooler temperatures during unpowered or lower powered operation (that is, during the REST time) as compared to continuously powering the catalyst at the run temperature of, for example, 350-600° C.

In a device, system or method hereof, the measured variable may be used to correct gas concentration output/readings in real-time. Below is a representative example of a formula for adjusting the sensitivity of the system.

$$S_t = S_o * (C_o / C_t * k)$$

In the above equation, $S_t$ is the sensitivity at a given time t; $S_o$ is the initial or previously determined sensitivity, $C_o$ is the initial or previously determined variable related to the Compare mode, $C_t$ is the variable measured at a given time t and k is a scaling factor constant. A lookup table may, for example, alternatively be used to related a change in the measured variable to a sensitivity correction.

Furthermore, the measured variable hereof may be used as a trigger to apply additional heat to the catalyst support structure to potentially remove inhibitors. Periodic measurement of the variable, analysis of the results thereof, correction of sensor output and/or application of additional heat may, for example, be effected by control system 300 (via, for example, an algorithm or algorithms stored in memory system 320 as software) in an automated manner without user intervention. The measurement of a variable (for example, voltage, current or resistance) and associated application of additional heat may be done in real time and offer not only a life and health aspect for the system, but a self-curing attribute. Moreover, if the sensor fails to "burn off" a contaminant, it can be determined that the contaminant is a poison. The user may be notified that the active element of the system has been poisoned (for example, via display system 210, alarm system 220 and/or other user interfaces). The "burn off" procedure described herein may, for example, be used in connection with any electronic interrogation of the active sensing element that is suitable to determine that a foreign material has contaminated the active sensing element.

Figure 9:
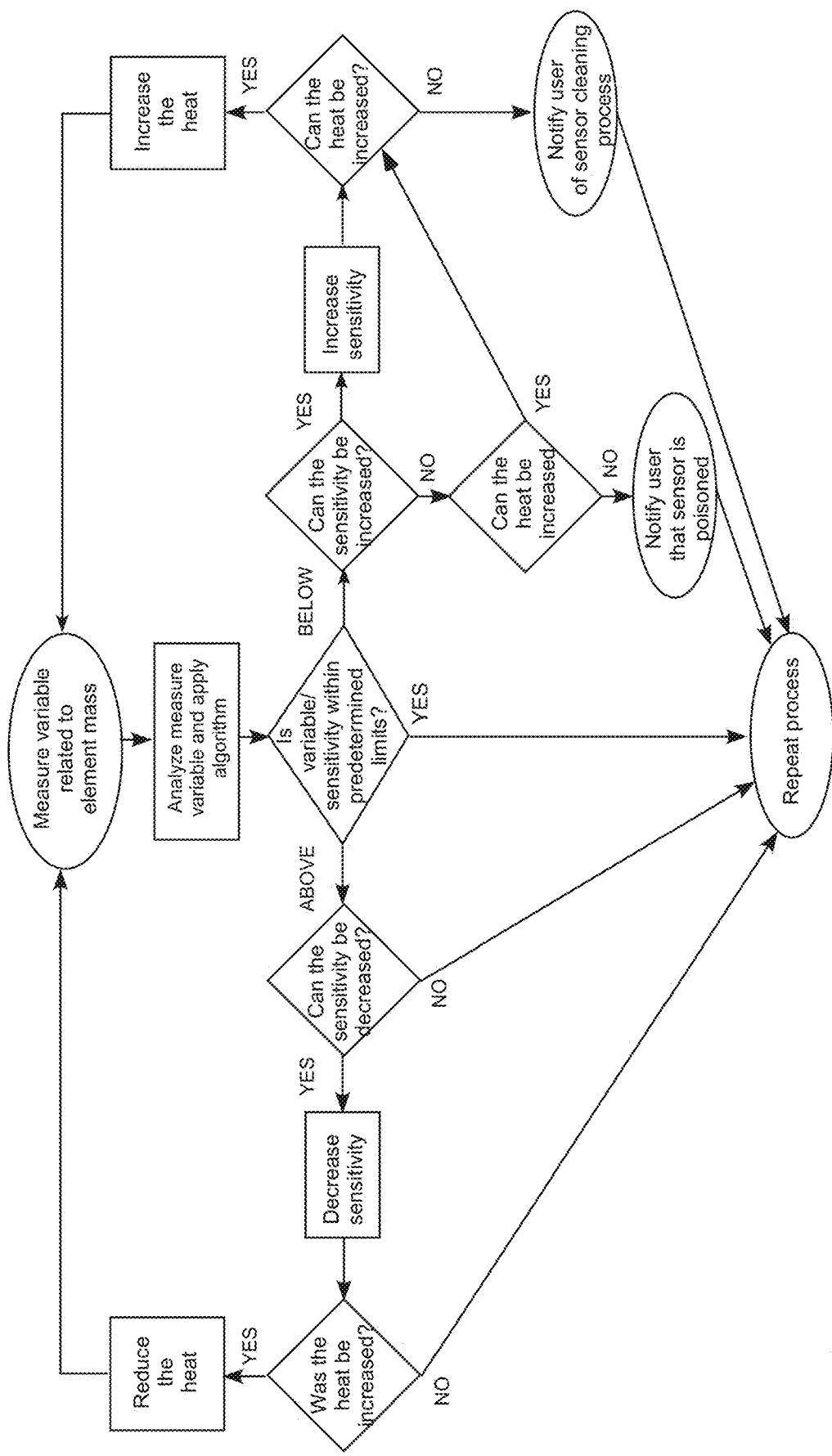
FIG. 9 illustrates a representative embodiment of methodology for operating a sensor hereof.

FIG. 9 illustrates an embodiment of an electronic interrogation or control algorithm or process hereof. In the embodiment of FIG. 9, each time a variable related to mass change in the sensing element is measured, it is evaluated. If the variable and/or a correction of sensitivity associated therewith is within normal limits (for example, +/−1% of a predetermined or threshold value), no corrections occur and the sequence repeats. If a non-conforming result is obtained (that is, the variable and/or correction is not within normal limits), different actions are taken depending upon whether sensitivity should be increased or decreased, which is dependent upon the measured variable. If the measured variable results in a need to increase the sensitivity (for example, associated with contamination of the sensing element), the algorithm will determine if the increase is within normal limits, and do so. If the increase is within normal limits, the system will attempt to increase the heat to burn off any inhibitors, and the user may, for example, be alerted that this "burn-off" or cleaning process is taking place. If the maximum thermal limit has already been applied, and the maximum correction has also been applied, then the user may, for example, be alerted that the sensing element has been poisoned. If the measured variable results in the need to decrease the sensitivity, the algorithm will determine if the decrease is within normal limits, and do so. If the decrease is within normal limits, the system will check to see if heat had been previously applied to attempt to burn off an inhibitor. If heat had been applied, the heat will be reduced. This control algorithm or a similar algorithm hereof may, for example, be an automated procedure carried out via the control system without the need for user intervention. The control algorithm may, for example, be embodied in software stored within memory system 320 and executed by processor(s) 310 of control system 306. In a number of embodiments, the combustible gas sensor is operative to detect the combustible gas analyte during the execution of the electronic interrogation, control algorithm or process.

The devices, systems and/or methods described herein can be used in connection with a variety of types of combustible gas sensors. Existing combustible gas sensors designs are readily modified to include a device or system hereof for measuring an variable related to mass change of one or more sensing elements thereof. For example, such devices, systems and/or methods can be used in connection with Micro-Electro-Mechanical Systems (MEMS), thin/thick film system, or other suitable micro- or nanotechnology systems such as, for example, described in U.S. Pat. No. 5,599,584 and/or U.S. Pat. No. 6,705,152.

The devices, systems and methods hereof may, for example, be used in connection with other devices, systems and methodologies for detecting poisoning or inhibiting of catalysts (including for example, electronic interrogations methodologies which do not require application of a test or other gas to the sensor). For example, devices, systems and methods disclosed in U.S. Patent Application Publication No. 2014/0273,263, the disclosure of which is incorporated herein by reference) may be used. In such devices, systems and methods, a variable related to the complex component of impedance, which is sometimes referred to as reactance, of the first sensing element (variables that may be measured include, but are not limited to, impedance, reactance, resonant frequency, a frequency dependent variable, inductance, capacitance, or the resistive components of inductance and/or capacitance). Changes in the measured variable over time provide are used to determine the operational status of the sensing element.

Impedance is defined by the formula $Z = R + jX$, wherein Z is the impedance. The real component of impedance Z is the resistance R, while the complex or imaginary component of impedance is the reactance X (wherein j is the imaginary unit). Both capacitive reactance $X_C$ and the inductive reactance $X_L$ contribute to reactance (or total reactance) according to the following formula $X = X_L - X_C$. In general, measurement of impedance or reactance (and/or variables related thereto) requires a variation in applied voltage or current. In the absence of an analyte, resistance of the sensing element remains constant over time, but the complex component of impedance (that is, reactance) varies as a function of sensing element operational state or functionality. Measuring a variable related to reactance may, for example, provide an indication that an inhibitor or poison has entered the catalyst support structure.

The foregoing description and accompanying drawings set forth embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A combustible gas sensor for detecting an analyte gas, comprising: a first element, the first element comprising a first electric heating element, a first support structure on the first electric heating element and a first catalyst supported on the first support structure, the combustible gas sensor further comprising electronic circuitry in electrical connection with the first element, the electronic circuitry being configured to operate in a first mode in which the first element is operated at a first temperature at which the first catalyst catalyzes combustion of the analyte gas, and in a second mode wherein the first element is operated at a second temperature which is below the temperature at which the first catalyst catalyzes combustion of the analyte gas but at which Joule heating of the first element occurs, the electronic circuitry being configured to measure a variable in the second mode related to a mass of the first element and to analyze a change in the variable to determine if poisoning or inhibiting of the catalyst of the first element has occurred.

2. The combustible gas sensor of claim 1 further comprising a second element comprising a second electric heating element and a second support structure on the second electric heating element, the electronic circuitry being in electrical connection with the second element and being configured to operate the second element at a third temperature which is lower than the temperature at which the first catalyst catalyzes combustion of the analyte gas in the first mode, and to operate the second element at a fourth temperature which is lower than the temperature at which the first catalyst catalyzes combustion of the analyte gas in the second mode, wherein the electronic circuitry is further configured to operate the second element to compensate for ambient conditions in the first mode and in the second mode.

3. The combustible gas sensor of claim 2 wherein the second temperature, the third temperature and the fourth temperature are below a temperature at which one or more predetermined catalyst inhibiting compositions or catalyst poisoning compositions are oxidized on the first support structure and the second support structure.

4. The combustible gas sensor of claim 2 wherein the fourth temperature is below the temperature at which the first catalyst catalyzed combustion of the analyte gas but above a temperature at which Joule heating of the second element occurs.

5. The combustible gas sensor of claim 2 wherein the second temperature, the third temperature and the fourth temperature are below 150° C.

6. The combustible gas sensor of claim 2 wherein the second temperature, the third temperature and the fourth temperature are below 90° C.

7. The combustible gas sensor of claim 5 wherein the second temperature is within 5% of the fourth temperature.

8. The combustible gas sensor of claim 5 wherein the second temperature is within 2% of the fourth temperature.

9. The combustible gas sensor of claim 5 wherein the variable is selected from the group consisting of voltage, current or resistance.

10. The combustible gas sensor of claim 5 wherein the first support structure and the second support structure comprises, independently, a porous, electrically insulating material.

11. The combustible gas sensor of claim 5 further comprising a control system in communicative connection with the electronic circuitry.

12. The combustible gas sensor of claim 11 wherein the control system is configured to alter an output of the combustible gas sensor based on the change in the measured variable.

13. The combustible gas sensor of claim 11 wherein the control system is configured to provide information to a user regarding the operational status of at least the first element based on a change in the measured variable.

14. The combustible gas sensor of claim 11 wherein the control system is configured to increase the temperature of the first element upon the change in the measured variable to attempt to burn off the foreign material.

15. The combustible gas sensor of claim 5 wherein the second element further comprises a second catalyst supported on the second support structure and the electronic circuitry is further configured to operate in a third mode in which the second element is operated at a fifth temperature at which the second catalyst catalyzes combustion of the analyte gas and in a fourth mode wherein the second element is operated at a sixth temperature which is below the temperature at which the second catalyst catalyzes combustion of the analyte gas and below a temperature at which the one or more predetermined catalyst inhibiting compositions or catalyst poisoning compositions are oxidized on the second support structure, but at which Joule heating of the second element occurs, the electronic circuitry being further configured to measure a second variable in the third mode related to a mass of the second element and to analyze a change in the second variable to determine if poisoning or inhibiting of the catalyst of the second element has occurred.

16. The combustible gas sensor of claim 15 wherein the electronic circuitry is further configured to operate the first element at a seventh temperature which is lower than the temperature at which the first catalyst catalyzes combustion of the analyte gas and below the temperature at which the one or more predetermined catalyst inhibiting compositions or catalyst poisoning compositions are oxidized on the first support structure in the third mode, and to operate the first element at an eighth temperature which is lower than the temperature at which the first catalyst catalyzes combustion of the analyte gas in the fourth mode, but at which Joule heating of the first element occurs, wherein the electronic circuitry is further configured to operate the first element to compensate for ambient conditions in the third mode and in the fourth mode.

17. A method of operating a combustible gas sensor for detecting an analyte gas, the combustible gas sensor including a first element, the first element including a first electric heating element, a first support structure on the first electric heating element and a first catalyst supported on the first support structure, and electronic circuitry in electrical connection with the first element, the method comprising: operating the electronic circuitry in a first mode in which the first element is operated at first temperature at which the first catalyst catalyzes combustion of the analyte gas, operating the electronic circuitry in a second mode wherein the first element is operated at a second temperature which is below the temperature at which the first catalyst catalyzes combustion of the analyte gas but at which Joule heating of the first element occurs, measuring a variable via the electronic circuitry in the second mode related to a mass of the first element, and analyzing a change in the variable to determine if poisoning or inhibiting of the catalyst of the first element has occurred.

18. The method of claim 17 wherein the combustible gas sensor further includes a second element including a second electric heating element and a second support structure on the second electric heating element, the method further comprising operating the second element at a third temperature which is lower than the temperature at which the first catalyst catalyzes combustion of the analyte gas in the first mode via the electronic circuitry, operating the second element at a fourth temperature which is lower than the temperature at which the first catalyst catalyzes combustion of the analyte gas in the second mode via the electronic circuitry, wherein the electronic circuitry operates the second element to compensate for ambient conditions in the first mode and in the second mode.

19. The method of claim 18 wherein the second temperature, the third temperature and the fourth temperature are below a temperature at which catalyst inhibiting compositions or catalyst poisoning compositions are oxidized on the support structure.

20. The method claim 18 wherein the fourth temperature is below the temperature at which the first catalyst catalyzes combustion of the analyte gas but above a temperature at which Joule heating of the second element occurs.

21. The method of claim 19 wherein the second temperature, the third temperature and the fourth temperature are below 150° C.

22. The method of claim 19 wherein the second temperature, the third temperature and the fourth temperature are below 90° C.

23. The method of claim 21 wherein the second temperature is within 5% of the fourth temperature.

24. The method of claim 21 wherein the second temperature is within 2% of the fourth temperature.

25. A combustible gas sensor for detecting an analyte gas, comprising: a first element, the first element comprising a first electric heating element, a first support structure on the first electric heating element and a first a catalyst supported on the first support structure, a second element comprising a second electric heating element and a second support structure on the second electric heating element, the combustible gas sensor further comprising electronic circuitry in electrical connection with the first element and the second element, the electronic circuitry being configured to operate in a first mode in which the first element is operated at a first temperature at which the first catalyst catalyzes combustion of the analyte gas, and in a second mode wherein the first element is operated at a second temperature which is below the temperature at which the first catalyst catalyzes combustion of the analyte gas but at which Joule heating of the first element occurs, the electronic circuitry further being configured to operate the second element to compensate for ambient conditions in the first mode and in the second mode to measure a variable in the second mode related to a mass of the first element, wherein a change in the variable is relatable to poisoning or inhibiting of the catalyst of the first element, wherein the second element is operated below a temperature at which one or more predetermined catalyst inhibiting compositions or catalyst poisoning compositions are oxidized on the second support structure in the first mode and in the second mode.

26. The combustible gas sensor of claim 25 wherein the second temperature and the temperature at which the second element is operated are below 150° C.

27. The combustible gas sensor of claim 25 wherein the second temperature and the temperature at which the second element is operated are below 90° C.

* * * * *

UNITED STATES PATENT AND TRADEMARK OFFICE
CERTIFICATE OF CORRECTION

PATENT NO. : 10,627,379 B2
APPLICATION NO. : 15/597933
DATED : April 21, 2020
INVENTOR(S) : Mark Flori Zanella, Sr., Meghan E. Swanson and Daniel D. Santoro, Jr.

Page 1 of 1

It is certified that error appears in the above-identified patent and that said Letters Patent is hereby corrected as shown below:

In the Specification
Column 9, Line 52 delete "element" and insert --an element--.
Column 10, Line 66 delete "less than 1.5 less" and insert --less than 1.5--.
Column 12, Line 29 delete "be dipped it into" and insert --may be dipped into--.
Column 13, Line 35 delete "or" and insert --of--.
Column 19, Line 40 delete "display system 210, alarm system 220" and insert --display system 330, alarm system 340--.
Column 20, Line 43 delete "provide".

Signed and Sealed this
Fourteenth Day of July, 2020

Andrei Iancu
*Director of the United States Patent and Trademark Office*